United States Patent [19]

Dempster

[11] Patent Number: 5,105,825
[45] Date of Patent: Apr. 21, 1992

[54] METHOD AND APPARATUS FOR VOLUME MEASUREMENT AND BODY COMPOSITION ESTIMATION

[75] Inventor: Philip T. Dempster, St. Helena, Calif.

[73] Assignee: Life Measurement Instruments, Davis, Calif.

[21] Appl. No.: 551,526

[22] Filed: Jul. 10, 1990

[51] Int. Cl.⁵ .............................................. A61B 5/103
[52] U.S. Cl. ........................................ 128/774; 73/149
[58] Field of Search ................... 128/774, 720; 73/149

[56] References Cited

U.S. PATENT DOCUMENTS

| | | | |
|---|---|---|---|
| 3,113,448 | 12/1963 | Hardway, Jr. et al. | 73/149 X |
| 3,511,237 | 12/1965 | Jaeger | 128/720 |
| 3,769,834 | 11/1973 | Fletcher et al. | 73/149 |
| 4,184,371 | 1/1980 | Brachet | 73/433 |
| 4,369,652 | 1/1983 | Gundlach | 73/149 |
| 4,561,298 | 12/1985 | Pond | 73/149 |
| 4,640,130 | 2/1987 | Sheng et al. | 73/149 X |
| 4,888,718 | 12/1989 | Furuse | 364/564 |

*Primary Examiner*—Max Hindenburg
*Attorney, Agent, or Firm*—Heller, Ehrman, White & McAuliffe

[57] ABSTRACT

Method and apparatus for volume measurement and body composition estimation provides an accurate, non-invasive estimation of the body volume and body composition of an object or body such as a human being. The present invention provides a first chamber with a door or closable means of entry through which an object or a subject may enter, along with a second chamber and means to cyclically perturb the volumes of the two chambers in a precisely complementary fashion. The present invention also measures the pressure in each of the chambers, controls in real time the volume perturbation and analyzes the pressure records so as to yield volume and body composition estimations.

19 Claims, 2 Drawing Sheets

FIG.—1

METHOD AND APPARATUS FOR VOLUME MEASUREMENT AND BODY COMPOSITION ESTIMATION

This invention was made with Government support under grant No. 1 R43 DK 42396-01 awarded by the National Institutes of Health. The Government has certain rights in the invention.

BACKGROUND OF THE INVENTION

The present invention relates to the field of body volume measurement, body composition estimation (fat as a percentage of body weight) and nutritional assessment. It relies on the well-known relationship between body density and body composition.

The measurement of body composition is important in the management of acute and subacute illnesses. Excessive body fat is associated with, and can have an adverse effect on, a number of disease processes in adults, including cardiovascular disease, diabetes, hypertension, pulmonary diseases, and kidney disease.

A variety of techniques are in use today, including measurement of skinfolds, bioelectric impedance, total body electrical conductance, and determination of body density by hydrostatic weighing (using Archimedes principle). All of these techniques are plagued by significant problems.

Skinfold measurement suffers from population-specific prediction equations, variations in fat patterning, and a requirement for significant technician training.

Bioelectric impedance measurement can be affected by the state of hydration and the temperature of the subject and surrounding environment.

Measurement of total body electrical conductance requires very expensive equipment and which occupies a large amount of space.

Hydrostatic weighing requires immersion in a tank of water which is difficult or impossible for many individuals. In addition, the necessary measurement of residual lung volume requires expensive apparatus, including a nitrogen or helium analyzer.

In addition, there is no suitable method for the assessment of dietary needs in premature infants. A non-invasive estimation of body composition would provide neonatologists with an important tool that is not now available.

Various investigators have attempted to estimate body volume using plethysmographic techniques, but generally the results have fallen short of the precision required for useful estimation of body composition in terms of fat and lean body mass.

Gundlach, U.S. Pat. No. 4,369,652, has achieved fairly good results, but that apparatus requires that the subject be wrapped in a down or polyester "cocoon." In addition, elaborate precautions to control temperature are required.

Gundlach's apparatus uses parallel pistons to produce volume changes in two chambers, with the difference in the pressures of the two chambers being measured. In distinction to the present invention, elaborate means are required to produce precisely proportional volume changes in the two chambers. Also, air circulation between the two chambers is impossible with parallel volume perturbation.

Brachet U.S. Pat. No. 4,184,371 describes a two-chamber body system in which parallel pistons perturb the chambers with one piston of variable displacement so that pressure perturbations can be equalized. No provision is made to take into account the differences in compressability of air in the chamber and air in the lungs. Therefore, there is little expectation that the necessary precision could be achieved by this system.

Sheng U.S. Pat. No. 4,640,130 describes a system in which the frequency of a Helmholz resonator is varied by inclusion of a subject in the body of the resonator. As with Brachet, no attempt is made to account for the different behavior of air in the lungs, resulting in poor accuracy.

Fletcher U.S. Pat. No. 3,769,834 describes a single chamber device to assess body volume changes in astronauts. Cyclical volume perturbation induces pressure changes in the chamber which are related to the volume of the chamber minus the volume of the astronaut. Fletcher's method includes external respiratory connections. Because a large acoustic leak exists through tissue coupling from the chamber to the interior of the lungs and thence through the airways to the outside of the chamber, this system could not achieve the required accuracy. Additionally, the output of such a device would vary with barometric pressure.

A variety of inventions exist for the measurement of tank volumes, liquid level in a tank, and the volumes of irregular objects, and the volume of meat samples. (cf Doshi U.S. Pat. No. 4,704,902, Parker, U.S. Pat. No. 4,474,061, Nienisi U.S. Pat. No. 4,770,033, Turner U.S. Pat. No. 4,112,738, Leger U.S. Pat. No. 3,487,698, Hardway U.S. Pat. No. 3,113,448, Hamilton U.S. Pat. No. 3,129,585, Taylor U.S. Pat. No. 3,282,115, Thyron U.S. Pat. No. 4,713,966, Keng U.S. Pat. No. 3,585,861, Pond U.S. Pat. No. 4,561,298). These references generally suffer from a variety of defects that make them unadaptable for body volume measurement with the precision required for body composition assessment. In particular, none of them have any provision in apparatus or computation to take into account the different behavior of air in the lungs and in the chamber at large.

Only Gundlach of the above cited references has demonstrated an understanding of the need to deal with the fact that air in the lungs exists in substantially isothermal conditions, in distinction to the other air in the chamber.

But Gundlach requires a cumbersome arrangement of down or polyester fiber surrounding the subject, elaborate means to insure proportional volume perturbation, and precautions to insure very constant temperature conditions, as well as elaborate precautions to nullify other temperature effects.

Therefore, a need exists for a practical, accurate and noninvasive apparatus to estimate body volume and body composition.

SUMMARY OF THE INVENTION

It is an object of the present invention to provide an accurate, non-invasive estimation of the body volume of an object such as a human being.

It is another object of the present invention to provide an accurate, non-invasive estimation of the body composition of a human being.

Briefly, in one preferred embodiment, the present invention provides a first chamber with a door or closable means of entry through which an object or a subject may enter, along with a second chamber, and means to cyclically perturb the volumes of the two chambers in a precisely complementary fashion. The present invention also includes means to measure the pressure in each of the chambers, means for controlling in real time the volume perturbation, and means for analyzing the pressure records so as to yield volume and body composition estimations.

In a further embodiment, the present invention includes means to circulate air between the two chambers so as to provide substantially constant atmospheric conditions in the two chambers in order to improve accuracy and repeatability.

In a still further embodiment, the present invention combines plethysmographic techniques for thoracic gas volume measurement to the aspects mentioned above, in order to refine and improve the accuracy of the body volume measurement.

Additional objects, advantages and novel features of the present invention will be set forth in part in the description which follows and in part become apparent to those skilled in the art upon examination of the following or may be learned by practice of the invention. The objects and advantages of the invention may be realized and attained by means of the instrumentalities and combinations which are pointed out in the appended claims.

BRIEF DESCRIPTION OF THE DRAWINGS

The accompanying drawings which are incorporated in and form a part of this specification illustrate and embodiment of the invention and, together with the description, serve to explain the principles of the invention.

DESCRIPTION OF THE PREFERRED EMBODIMENT

Reference will now be made in detail to the preferred embodiment of the present invention, an example of which is illustrated in the accompanying drawings. While the invention will be described in conjunction with the preferred embodiment, it will be understood that it is not intended to limit the invention to that embodiment. On the contrary, it is intended to cover alternatives, modifications and equivalents as may be included within the spirit and scope of the invention as defined by the appended claims.

Figure 1:
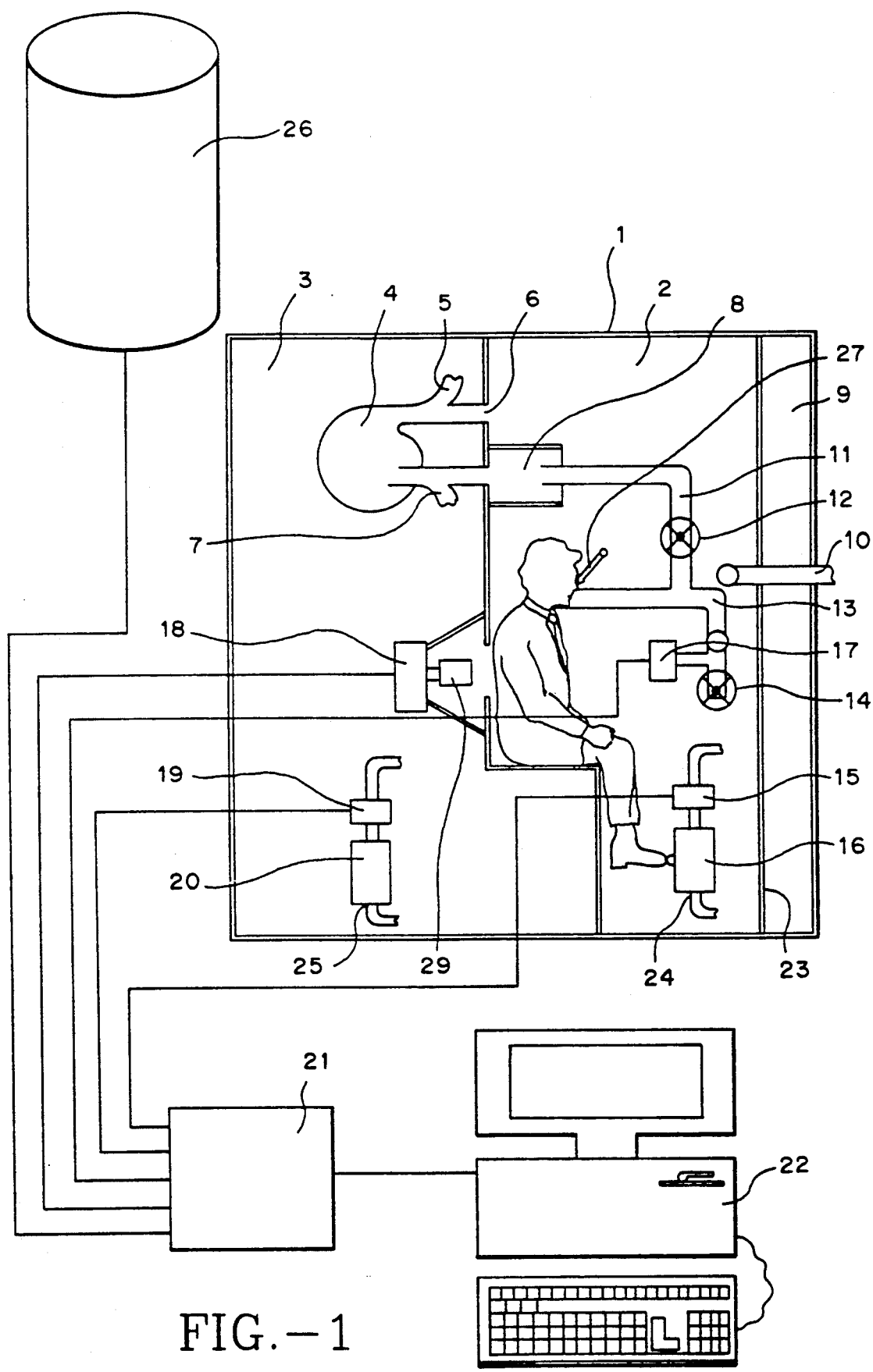
FIG. 1 is a diagramatic view of the apparatus according to the present invention.

Apparatus:

FIG. 1 shows a diagramatic view of the apparatus according to the present invention. It includes a single structure 1 which contains reference chamber 3, test chamber 2, door 9 for ingress and egress, door seal 23, and latch 10. Attached to and mounted within structure 1 are various items which will be described. The structure may be constructed of any suitably rigid material, such as plywood, molded fiberglass, aluminum and the like, and may contain transparent panels constructed of a material such as glass, plexiglass or polycarbonate.

It is not essential to the operation of the invention that the two chambers comprise a single structure. The door seal 23 may be constructed of any suitably compressible material which will insure a substantially airtight seal between the interior of test chamber 2 and the exterior environment.

The apparatus includes two pressure transducers 15 and 19. In a preferred embodiment, these are differential, low pressure transducers of the piezo-resistive type. The first input of transducer 15 communicates with test chamber 2 and the second input is connected to an acoustic low pass filter 16, which comprises a chamber with a highly restrictive input 24. This input 24 also communicates with test chamber 2. Similarly, transducer 19 has one input communicating with reference chamber 3 and the other input connected to lowpass filter 20 whose input 25 communicates with reference chamber 3.

The effect is that transducers 15 and 19 respond to varying pressure in chambers 2 and 3 respectively, while rejecting steady state pressure components. The purpose is to make the transducers immune to ambient pressure changes such as would be caused by closing a door, wind through an open window, or some ventillation systems. However, useful results could be obtained using simple gauge type transducers whose reference is to ambient. It should be understood that other types of transducers such as dynamic microphones, piezoelectric microphones, capacitive transducers or differential transformer transducers could also be used.

In the preferred embodiment, when a subject is inside test chamber 2, he is asked to breath into air passage 13, while his nose is pinched closed by clamp 27. Transducer 17 has its input connected to the interior of this airway. Transducer 17 may be similar to transducers 15 and 19, but should be sized for higher pressure excursions. The reference port of transducer 17 may be open to ambient conditions without detriment to performance, because the pressures measured are significantly larger than those measured by transducers 15 and 19.

Air passage 13 bifurcates into two passages, one of which exits into the interior of test chambers 2 through valve 12, and one which exits to ambient through valve 14 By positioning the two valves 12, 14, the subject may breathe air external to the chamber, internal to the chamber, and have his air passage entirely occluded. Although as shown these valves are manually operated, they could be controlled by computer 22.

During a portion of the testing, it is not absolutely required that the subject breath into the airway system or be wearing a nose clamp; however, in the preferred embodiment, such is the case.

Air pump 4 is arranged so as to draw air from both chambers 2, 3, into its inlet, and to expel air into both chambers 2, 3. Thereby, each chamber is provided with an air source which is mixture of the air from both chambers. The action of this pump tends to create equal conditions in both chambers, in the sense that gas composition and temperature in each chamber will tend towards a common condition. Aiding this situation is the fact that the interior air passage 11 exits in the vicinity of the pump 4 inlet, so that it is substantially true that exhaled air will be discharged into both chambers. It is also a feature of the pump arrangement that air is circulated between the two chambers without creating a pressure difference between the two chambers.

The connections of the pump 4 create an air passage between chambers 2 and 3. It is desirable that this passage be kept fairly small. Therefore, the use of small passages and higher pressures is preferred. Pump 4, for example, may be a centrifugal type, of the same general design as is found in vacuum cleaners. However the need for tolerable noise levels puts some limits on the speed at which such a pump may be run.

It should be understood that while the air pump is a feature of the invention that improves accuracy and reliability, a useful instrument could be constructed without it. Also, other air pump arrangements would produce the same effect. For example, two pumps could be arranged between the two chambers, one pumping from chamber 2 to 3 and the other from chamber 3 to 2. Additionally, a single pump with a relatively large return hole could be made to work.

An oscillating diaphragm means 18 is interposed between the reference chamber 3 and the test chamber 2. For example, means 18 may comprise a 15" dynamic loudspeaker. Preferably, such a means should have a very repeatable position (some loudspeakers may fail to provide sufficient repeatability).

One method of insuring such repeatability is to attach a position sensing element 29 between the cone of the loudspeaker and its frame. That element may be an LVDT (Linear Variable-Differential Transducer)-type transducer or it may be of some other principle such as a variable capacitance. The transducer and the loudspeaker may be combined with an amplifier so that the loudspeaker is driven by an error signal in a classical servo system. Such systems are well understood and could be developed by one skilled in servo system art.

Although the preferred embodiment includes such a servo system, some loudspeakers may not require such a system to perform adequately. Also entirely different means could suffice. For example, to a person skilled in the art, the development of a piston or diaphram operated from a motor and a crankshaft to achieve substantially the same function would be understood.

The effect of the oscillating diaphram 18 on the chambers 2 and 3 is to produce an equal and opposite oscillatory change in the volumes of the two chambers.

In FIG. 1, calibration volume 26 is a structure which has a precisely known volume. It may be constructed of a variety of materials, but must rigidy resist deformation by external air pressure. For ease of handling, it is likely to be hollow. For example, 26 could comprise an aluminum tube with a rigid in each end. Because changes in temperature and barometric pressure will otherwise produce imbalance between interior and exterior pressure, possibly resulting in deformation and volume change, a method to allow equilibration is desirable. For example, a valve may be left open except when in use, or a very small leak may be intentionally introduced between the interior and the exterior.

The electronics and interface package 21 of FIG. 1 comprises signal conditioning for the three pressure transducers, amplifier and servo system electronics for the loudspeaker and position transducer, analog to digital conversion of the signals from the three pressure transducers, and digital to analog conversion for creation of a command signal for the loudspeaker servo system. Package 21 includes a programmable timer which is attached to an interrupt of computer 22. Package 21 also contains the interface to the data bus of computer 22. The design of such an interface is well known to someone skilled in the art, and examples of such interfaces are found in industrial control, laboratories and elsewhere.

Appropriate software allows the computer 22 to drive the loudspeaker, read data from the three transducers, to analyze the data in order to provide volume measurement and body composition estimation.

Now that the apparatus according to the present invention has been described in conjunction with FIG. 1, measurement methods will now be described.

Two measurement methods are used in the course of estimating whole body volume. The first method measures the apparent volume of the subject, as if a person were a simple object with a relatively smooth surface. The second method estimates thoracic gas volume. This volume is used to develop a correction to the first measurement, because of the fact that the air interior to the lungs behaves differently than the air in the chambers.

The ratio of the volumes of chambers 2 and 3 may now be determined using the apparatus already described. Assume door 9 is closed, sealing chamber 2. Now suppose that diaphragm means 18 is made to oscillate sinusoidally under command by computer 22.

This oscillation could be at a frequency of 3 Hz, for example, although there is no particular significance to the exact frequency chosen. But a wavelength at the frequency chosen should be large compared to the dimensions of the chamber. The frequency should be low enough so that the pressure in the interior of the lungs is in substantial equilibration with the pressure in the chamber. This equilibration occurs due to air movement in and out of the lungs as well as deformation of the tissue between the chamber and the interior of the lung.

The oscillation will produce a complementary volume perturbation in the two chambers which is precisely equal in magnitude but opposite in sign. It is useful to consider this perturbation as if an amount of air were removed from one chamber and added to the other by the movement of the diaphram. Because the pressure changes induced are very small, resulting in no significant change in density of the gas in the two chambers, this analysis is very close to exact. It can now be seen that air that leaks between the two chambers through the air circulation system do not disturb the fact that volume perturbation of the two chambers is equal but complementary.

The air in each chamber compresses and rarifies in an oscillatory fashion under substantially adiabatic conditions. Therefore, the pressure changes inversely with approximately the 1.4th power of the proportional volume change. Because the pressure changes are very small, it is true to a close approximation that the pressure changes are 1.4 times the proportional volume changes.

Now an estimate of the ratio of the two chambers is prepared, using the signals from transducers 15 and 19. By the considerations expressed above, if P1 is the magnitude of the pressure fluctuation measured by transducer 15 and P2 is the magnitude of the pressure fluctuation of transducer 19, V1 is the volume of chamber 2 and V2 is the volume of chamber 3, it is expected that V1/V2=P2/P1 (it should be noted that the 1.4 factor does not need to appear in this equation, because it would be found in both the numerator and the denominator of the right hand side).

Because it is desirable that the present invention be accurate, repeatable and as immune to electrical and acoustic noise as possible, the preferred embodiment uses a more sophisticated analysis than is described above. A number of cycles are averaged, using a large number of sample points. These averages are analyzed for their fundamental (3 Hz) Fourier coefficients. These coefficients are then analyzed so as to detect the ratio of 3 Hz energy that is in phase.

It is a consequence of this analysis, that the ratio now computed is negative, because the pressure fluctuations are of opposite sign in the two chambers. This is of no importance, as will be seen.

The task of measuring the volume of an object with a relatively simple and smooth surface will now be described. Placing the object in chamber 1 and closing the door reduces the volume of the chamber by an amount equal to the volume of the object. In measuring the ratio of the two chamber volumes, the volume of the object is equal to the change in ratio times the volume of chamber 3.

What follows is a more practical procedure utilizing calibration volume 26. Taking the measured ratio as the output of a volume measuring transducer, a 2-point calibration may be used to standardize its output. First measuring with empty chambers, and second with the calibration volume in chamber 2, a baseline and a scale factor may be computed to make the system read directly in whatever units chosen.

Figure 2:
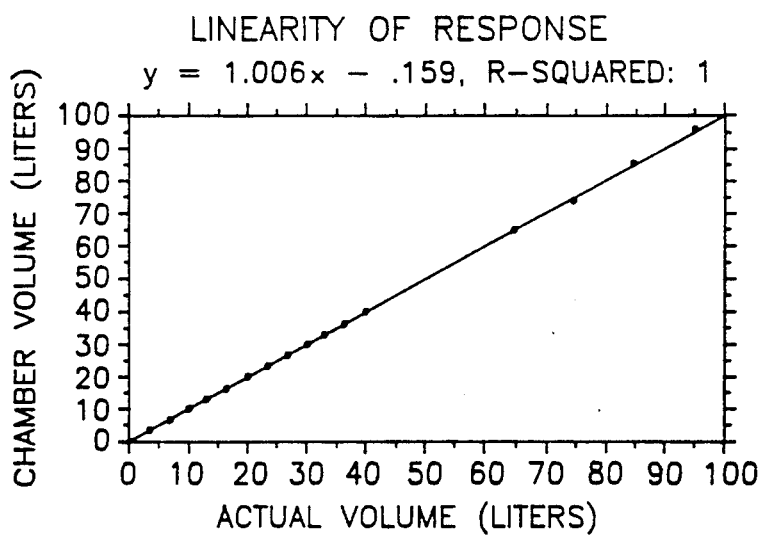
FIG. 2 is a graph demonstrating the linearity and accuracy of the present invention.

The practical use of a two-point calibration system assumes a high degree of linearity of the system. In fact, volume errors need to be well under 1% in order to have a useful system for estimation of body composition. The linearity of the invention is illustrated in FIG. 2.

Now suppose it is desired to measure the volume of an object with a complex surface. An example of such an object is a human subject. The surface of a human includes the interior of the lungs. Air in the lungs is in intimate contact with tissue which acts as a heatsink. Therefore, air in the lungs is not compressed under adiabatic conditions but under isothermal conditions. As such, its pressure varies inversely with the 1st power of volume change rather than the 1.4th power. For small perturbations, the air in the lungs is 40% more compressable than air in the box.

This factor must enter into a useful analysis of body volume. Otherwise the magnitude of the error introduced will produce substantially erroneous estimations of body composition. Although thoracic volume varies due to normal breathing, if the test extends over a few breathing periods, it suffices to know how much air is in the lungs as an average.

There are three ways this volume may be estimated.

The first is by computation using tables of normal volumes. This method introduces uncertainty which compromises the accuracy of the present invention. However, because such a method will still allow longitudinal comparison for a given subject, it may be useful in some applications.

The second method is to measure this volume using one of a variety of standard techniques and apparatus used in pulmonary function laboratories. For example, measurement of residual volume by a gas dilution technique combined with standard spirometric techniques allows estimation of average thoracic gas volume. When this information is available, it is an improvement over normal tables. But in general the need for such additional apparatus is a disadvantage. In fact, one of the features of the present invention is that such additional instrumentation such as is required by underwater weighing is not required.

The third method is to use the apparatus already described to estimate this volume. The method used is somewhat similar in concept to the method by which the ratio of the volumes of the two chambers was estimated, only in this case the test chamber is the interior of the lungs, the reference chamber is the interior of the invention, and the moveable diaphram is replaced by volitional effort on the part of the subject.

If subject breathing is occluded by closing valves 14 and 12, there is essentially no airflow in and out of the lungs. Therefore, the pressure in air passage 13 should be substantially identical to the pressure in the lungs. This pressure is monitored by transducer 14. If the subject is asked to cyclically vary this pressure, principally by tightening and releasing his or her diaphram, the thoracic gas volume will vary according to Boyle's law.

At the same time, this volume variation appears as a complementary volume change in chamber 2, resulting in a pressure change measured by transducer 15. This latter change is approximately 40% greater than expected by Boyle's law, as already seen.

If P1 is the change in lung pressure, Pt is the change in chamber 2 pressure, V1 is lung volume, and Vc is chamber volume - subject volume, the following relationship holds:

$$(1.4 V1)/Vc = -Pt/P1 \quad (1)$$

In the preferred embodiment, those ratios are computed over a number of cycles of pressure variation, using a method in which the pressure changes are analyzed for their correlated components. As an example, the measurement period may be three seconds. It would also be possible to make a number of measurements of much shorter duration.

In practice, there is some airleak between chamber 2 and chamber 3. Therefore the signal from transducer 19 must be added to the signal from transducer 17, with an appropriate scaling factor.

The method by which the lung volume measurement is calibrated in the preferred embodiment will now be described. By reference to equation (1) it may be seen that it is sufficient to find the volume of chambers 2 with the subject in it and the volume of chamber 3.

Each of the chambers 2 and 3 along with their transducers 17 and 19, may be thought of as detectors of gas volume change. As a small amount of gas is added to or subtracted from the chamber, there is an associated pressure change which results in transducer output. The ratio of the sensitivities of the transducer-chamber pairs is what is being measured each time a calibration of empty chambers using diaphragm 18 is made.

The change in this ratio using known calibration volume 26 is also measured. Each time a pressure fluctuation is induced in chamber 2 by diaphragm 18 without a subject being in the chamber, analysis of the records of transducer 17 and transducer 15 allow a gain factor to be developed for transducer 17 so that its output will be the same as transducer 15. An example of how this may be done is in the appended software.

In light of the interrelationship between transducer gain and chamber volume, and for expository simplicity, it will be assumed that the single variable is chamber volume.

The volume of chamber 3 may be calculated as follows: it has already been seen that the ratio of the volume of chamber 2 to chamber 3 may be calculated. Let R1 be the ratio with chamber 2 empty and R2 the ratio with the chamber containing calibration volume 26, giving the equations:

$$V1 = R1 V2 \qquad (2)$$

and $$V1 = Vc = R2 V2. \qquad (3)$$

where V1 is the volume of chamber 2, V2 is the volume of chamber 3, and Vc is the volume of the calibration volume. It may be seen that $$V2 = Vc / (R1 - R2) \qquad (4)$$

It remains to find the volume of the subject so that it may be subtracted from V1. That volume may be approximated by body weight if volume is measured in liters and weight in kilograms. Other methods would also be possible, including algebraic techniques which would yield a unique solution such that the thoracic volume calculated yields the body volume used in the calculation of thoracic volume.

Figure 3:
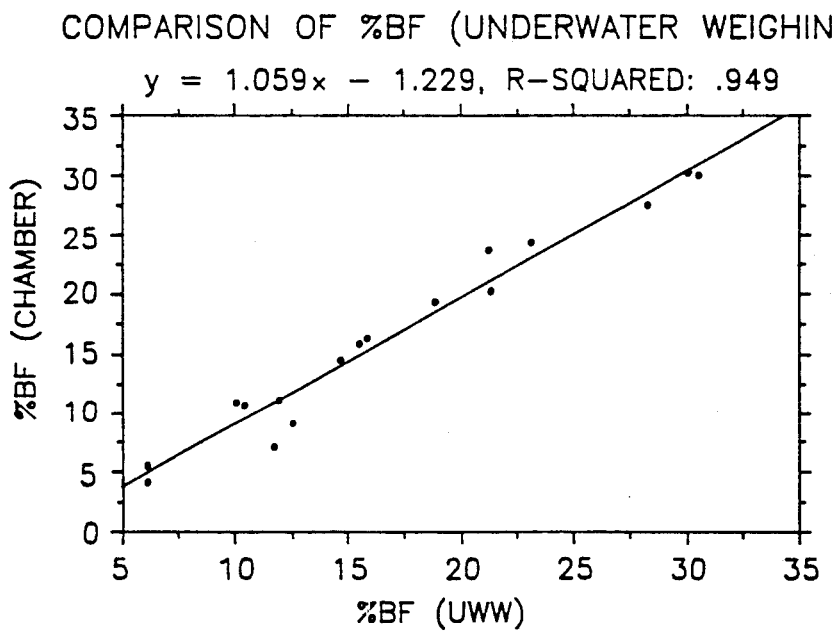
FIG. 3 is a graph demonstrating agreement between the present invention and underwater weighing.
Figure 4:
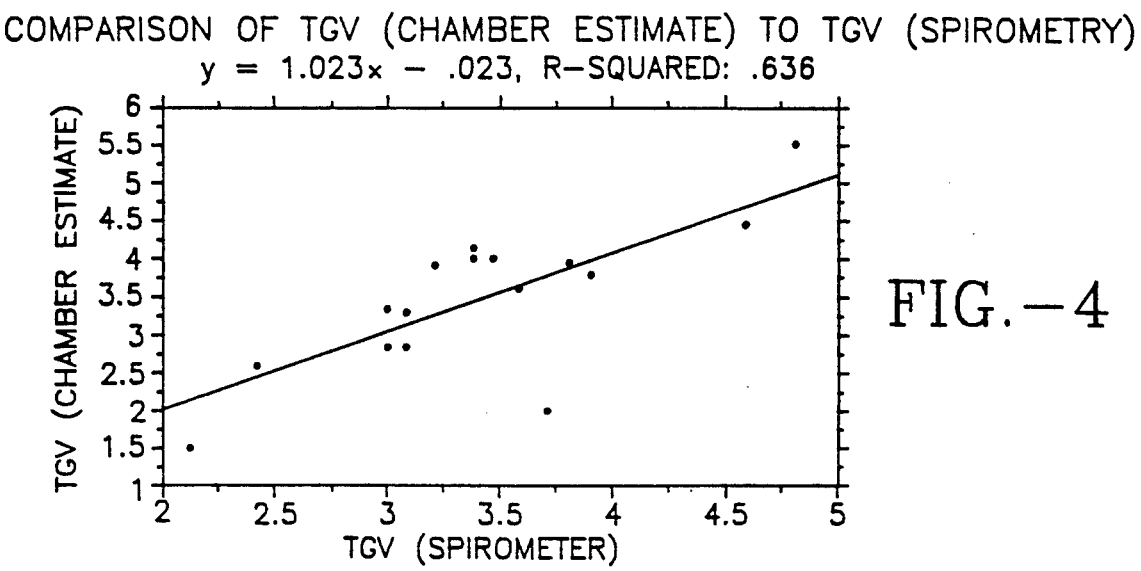
FIG. 4 is a graph demonstrating agreement between the present invention's measure of thoracic gas volume and measures yielded by spirometric and gas dilution techniques.

FIGS. 3 and 4 show graphs demonstrating agreement between the present invention and prior art techniques. More specifically, FIG. 3 is a graph demonstrating agreement between the present invention and underwater weighing, and FIG. 4 is a graph demonstrating agreement between the present invention's measure of thoracic gas volume and measures yielded by spirometric and gas dilution techniques.

The foregoing description of the preferred embodiment of the invention has been presented for purposes of illustration and description. It is not intended to be exhaustive or to limit the invention to the precise form disclosed, and many modifications and variations are possible in light of the above teaching. The preferred embodiment was chosen and described in order to best explain the principles of the invention and its practical applications to thereby enable others skilled in the art to best utilize the invention and various embodiments and with various modifications as are suited to the particular use contemplated. It is intended that the scope of the invention be defined only by the claims appended hereto.

What is claimed is:

1. A body volume measuring device comprising
   a first chamber,
   a second chamber,
   said first chamber having a sealable door for ingress and egress of a body, wherein the volume of said body is to be measured within said first chamber when said door is sealed, said first chamber having a first pressure sensing means, and said second chamber having a second pressure sensing means,
   control means,
   means for producing a complementary change in the volumes of said two chambers without equalizing pressure variations of said two chambers,
   said first and second pressure sensitive means responsive to the change in the volumes for producing respective outputs representative thereof,
   means interconnecting said first and second pressure sensing means and said means for producing with said control means,
   said control means including means responsive to the outputs of said pressure sensing means for providing volume estimates of said body.

2. A device as in claim 1 wherein said control means include computer control means.

3. A device as in claim 1 wherein said means for producing include oscillating volume varying means.

4. A device as in claim 3 wherein said oscillating volume varying means produce an equal and opposite sinusoidal oscillatory change in the volumes between said two chambers.

5. A device as in claim 4 wherein said first and second pressure sensing means are responsive to the equal and opposite change in the volumes between said two chambers.

6. A body volume measuring device as in claim 1 further including means for circulating air between said two chambers.

7. A body volume measuring device as in claim 6 including an airway through which a subject may breathe, connected to the interior of the first chamber, in such a fashion that a substantial portion of exhaled gas is circulated by the air circulation means.

8. A body volume measuring device as in claim 1, including an airway through which a subject may breathe, means to interrupt that breathing, said airway containing a pressure sensing means to communicate with said control means.

9. A body volume measuring device as in claim 1 further including a precise calibration volume within the interior of said first chamber.

10. In a body volume measuring device having a first chamber and a second chamber, said first chamber having a sealable door for ingress and egress of a body, the volume of which is to be measured within said first chamber when said door is sealed, said first chamber having a first pressure sensing means, and said second chamber having a second pressure sensing means, the method comprising the steps of
    producing a complementary change in the volumes of said two chambers such that said first and second pressure sensing means are responsive to the change in the volumes to produce respective outputs representative thereof without equalizing pressure variations of said two chambers,
    producing in response to the outputs of said pressure sensing means volume estimates of said body.

11. A method of measuring a volume as in claim 10 in which the volume is placed in the first chamber through the door and the door closed,
    producing complementary pressure changes in the two chambers,
    sensing the pressure changes,
    estimating the relative volume of the two chambers, and
    estimating by assessing the effect of said body on the volume of the chamber containing it.

12. A method as in claim 11 in which the volume measured has a complex surface such as a human being, and the effects of the gas volume in contact with that complex surface are used in the estimation of the volume.

13. A method as in claim 12 including averaging over many cycles to reduce the effects of noise and computing Fourier coefficients representative of said signal in order to reject harmonic components of the signal and to allow comparison only of the in-phase energy.

14. A method as in claim 13 in which a two-point calibration technique using a standard volume is employed comprising
    measuring the volume ratio of the two chambers with the chambers empty, measuring the volume ratio of the two chambers with the chamber with a door containing the calibration volume, deriving a baseline and scale factor and applying to the ratio number to read in volume units.

15. A method as in claim 14 in which accuracy and repeatability is enhanced by circulating air between the two chambers to maintain substantially identical compression and expansion characteristics under adiabatic conditions.

16. A method using apparatus as in claim 15 to estimate thoracic gas volume by the steps of occluding breathing for a short period of time, having the subject cooperate by producing a series of pressure fluctuation in the airways of the subject, measuring those pressure fluctuations, measuring the complementary pressure fluctuations in the two chambers, and estimating thoracic volume.

17. A method as in claim 16 for estimating thoracic volume in which calibration of the system is accomplished by cyclical complementary volume perturbation of the two chambers empty and comparison of the pressure perturbations that result in each chamber, comparison of the airway pressure record and the first chamber pressure record in order to standardize the airway pressure measurement to the first chamber pressure record, cyclical complementary volume perturbation of the two chambers with the first chamber containing the calibration volume and comparison of the pressure perturbations that result in each chamber, using the pressure records to calculate the volumes of the two chambers, using standardization of an airway pressure record to the first chamber pressure record, first chamber volume, and second chamber volume in order to yield a calibrated output of thoracic volume.

18. A method as in claim 17 in which thoracic gas volume estimation is combined with body volume estimation together to provide an estimation of body volume in which a correction for the effects of thoracic gas is made.

19. A method as in claim 18 including the steps of entry of body weight and estimating percent fat body.

* * * * *